United States Patent
Appenzeller et al.

(10) Patent No.: US 9,510,876 B2
(45) Date of Patent: Dec. 6, 2016

(54) INTRAMEDULLARY FIXATION SYSTEM

(71) Applicant: DePuy Synthes Products, Inc., Raynham, MA (US)

(72) Inventors: Andreas Appenzeller, Oberdorf (CH); Daniel Fluri, Oberdorf (CH)

(73) Assignee: DePuy Synthes Products, Inc., Raynham, MA (US)

(*) Notice: Subject to any disclaimer, the term of this patent is extended or adjusted under 35 U.S.C. 154(b) by 266 days.

(21) Appl. No.: 13/974,310

(22) Filed: Aug. 23, 2013

(65) Prior Publication Data
US 2014/0058391 A1    Feb. 27, 2014

Related U.S. Application Data

(60) Provisional application No. 61/692,673, filed on Aug. 23, 2012, provisional application No. 61/710,830, (Continued)

(51) Int. Cl.
*A61B 17/72*    (2006.01)

(52) U.S. Cl.
CPC ........... *A61B 17/72* (2013.01); *A61B 17/7208* (2013.01); *A61B 17/7258* (2013.01); *A61B 17/7283* (2013.01); *A61B 17/7291* (2013.01)

(58) Field of Classification Search
CPC . A61B 17/7266; A61B 17/72; A61B 17/7208; A61B 17/7258; A61B 17/7225
See application file for complete search history.

(56) References Cited

U.S. PATENT DOCUMENTS

| 4,429,690 A | 2/1984 | Angelino-Pievani |
| 4,467,793 A * | 8/1984 | Ender .............. 606/62 |

(Continued)

FOREIGN PATENT DOCUMENTS

| DE | 202005019277 | 2/2006 |
| EP | 0401650 | 12/1990 |

(Continued)

OTHER PUBLICATIONS

International Patent Application No. PCT/US2013/056345: International Search Report dated Oct. 23, 2013, 10 pages.

(Continued)

*Primary Examiner* — Eduardo C Robert
*Assistant Examiner* — Julianna N Harvey
(74) *Attorney, Agent, or Firm* — Baker & Hostetler LLP

(57) ABSTRACT

An intramedullary fixation system is configured to be fixed to first and second bone segments that are separated by a defect. The system includes an intramedullary fixation member that includes first and second wire segments that are twisted about each other so as to define a plurality of intersections. A distal one of the intersections is separable, such that rotation of the fixation device in a medullary canal causes bone material in the medullary canal to apply a counterforce to the wire segments that causes the distal intersection to separate, thereby driving respective distal ends of the wire segments into the bone segment, such that subsequent movement of the intramedullary fixation member a toward the first bone segment causes the second bone segment to move toward the first bone segment. The intramedullary fixation system can further include a fixation clip that anchors the intramedullary fixation member to the first bone segment.

27 Claims, 5 Drawing Sheets

Related U.S. Application Data filed on Oct. 8, 2012, provisional application No. 61/786,937, filed on Mar. 15, 2013.

(56) References Cited

U.S. PATENT DOCUMENTS

| | | | |
|---|---|---|---|
| 5,281,225 A * | 1/1994 | Vicenzi | 606/62 |
| 5,324,307 A | 6/1994 | Jarrett et al. | |
| 5,725,532 A * | 3/1998 | Shoemaker | 623/1.11 |
| 5,913,896 A * | 6/1999 | Boyle et al. | 623/1.15 |
| 6,203,545 B1 | 3/2001 | Stoffella | |
| 6,506,191 B1 | 1/2003 | Joos | |
| 6,558,388 B1 | 5/2003 | Bartsch et al. | |
| 7,776,076 B2 | 8/2010 | Grady et al. | |
| 8,172,884 B2 | 5/2012 | Bouman | |
| 8,343,152 B2 | 1/2013 | Gonzalez-Hernandez | |
| 2003/0153918 A1 | 8/2003 | Putnam et al. | |
| 2004/0236170 A1* | 11/2004 | Kim | 600/16 |
| 2005/0101961 A1 | 5/2005 | Huebner et al. | |
| 2005/0136764 A1* | 6/2005 | Sherman et al. | 442/103 |
| 2005/0261688 A1 | 11/2005 | Grady, Jr. et al. | |
| 2006/0009771 A1 | 1/2006 | Orbay et al. | |
| 2006/0189992 A1 | 8/2006 | Medoff | |
| 2006/0235399 A1 | 10/2006 | Carls et al. | |
| 2006/0276793 A1 | 12/2006 | Berry | |
| 2007/0173834 A1 | 7/2007 | Thakkar | |
| 2008/0065074 A1* | 3/2008 | Yeung | A61B 17/7032 606/269 |
| 2008/0188899 A1 | 8/2008 | Bottlang et al. | |
| 2008/0269745 A1* | 10/2008 | Justin | 606/62 |
| 2008/0281363 A1 | 11/2008 | Ullman et al. | |
| 2010/0036430 A1 | 2/2010 | Hartdegen et al. | |
| 2011/0009912 A1 | 1/2011 | Gonzalez-Hernandez et al. | |
| 2011/0257685 A1 | 10/2011 | Hay et al. | |
| 2011/0270312 A1* | 11/2011 | Assell et al. | 606/256 |
| 2011/0282393 A1 | 11/2011 | Gerlach et al. | |
| 2012/0004690 A1 | 1/2012 | Gonzalez-Hernandez | |
| 2012/0136396 A1 | 5/2012 | Baker et al. | |
| 2012/0330365 A1 | 12/2012 | Lin et al. | |
| 2014/0039561 A1 | 2/2014 | Weiner | |
| 2014/0058455 A1 | 2/2014 | Appenzeller et al. | |
| 2014/0058510 A1 | 2/2014 | Appenzeller et al. | |
| 2015/0018889 A1 | 1/2015 | Schneider | |
| 2015/0223853 A1 | 8/2015 | Appenzeller et al. | |

FOREIGN PATENT DOCUMENTS

| | | |
|---|---|---|
| EP | 0743045 | 11/1996 |
| EP | 0873718 | 10/1998 |
| EP | 0882431 | 12/1998 |
| FR | 2722545 | 1/1996 |
| FR | 2728155 | 6/1996 |
| WO | WO 87/02572 | 5/1987 |
| WO | WO 98/33448 | 8/1998 |
| WO | WO 2012/103164 | 8/2012 |

OTHER PUBLICATIONS

International Patent Application No. PCT/US2013/056367: International Search Report dated Oct. 23, 2013, 10 pages.
International Patent Application No. PCT/US2013/056374: International Search Report dated Nov. 5, 2013, 10 pages.
International Patent Application No. PCT/US2013/056348: International Search Report dated Jan. 17, 2014, 16 pages.
International Patent Application No. PCT/US2013/056348: Invitation to Pay Additional Fees dated Oct. 23, 2013, 6 pages.
U.S. Appl. No. 14/422,844, filed Feb. 20, 2015, Appenzeller.

* cited by examiner

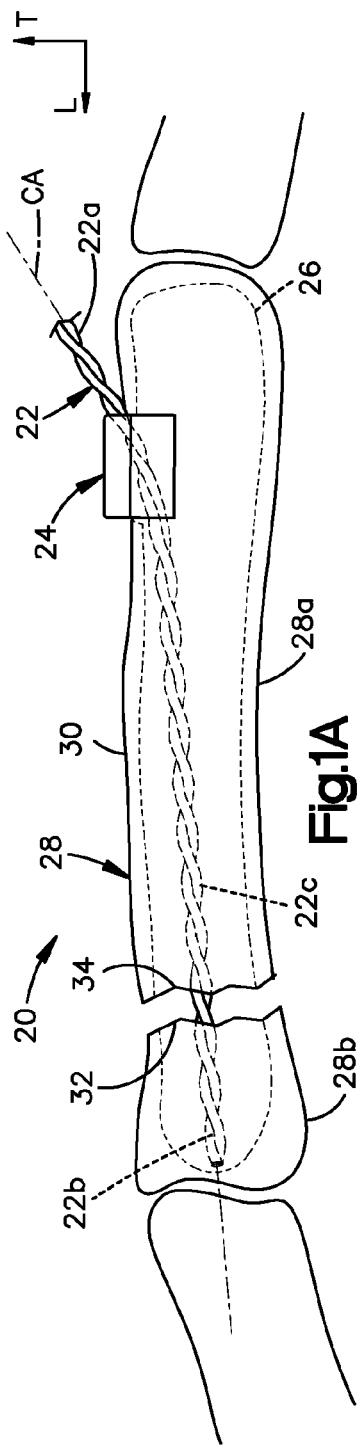
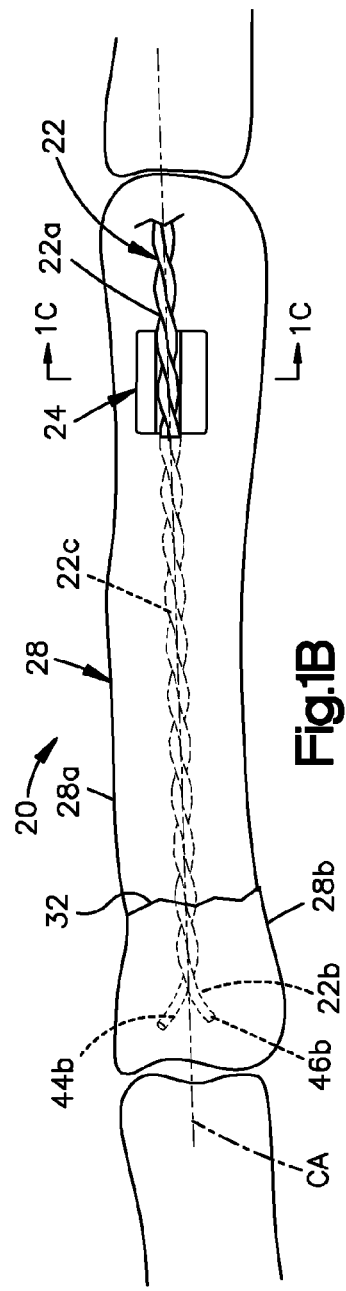
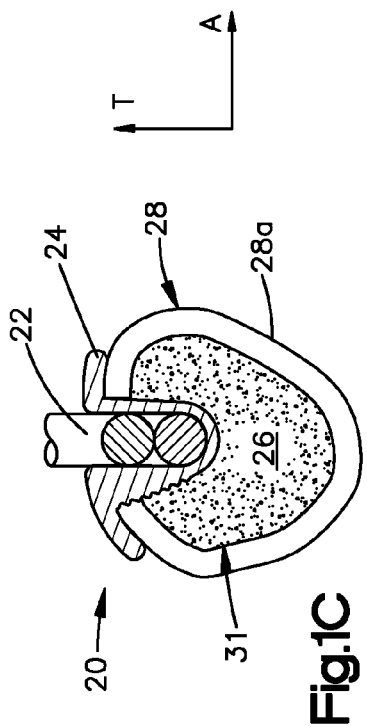

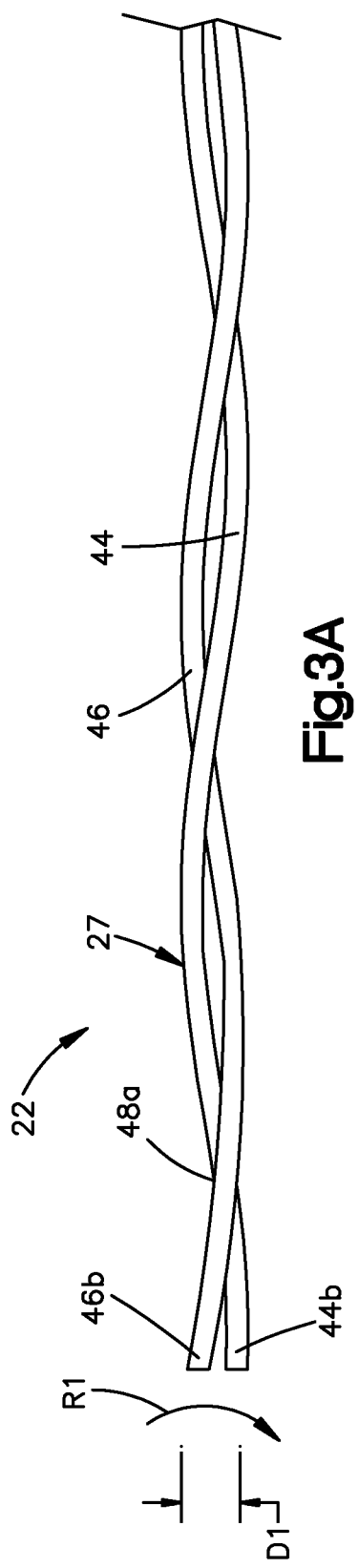
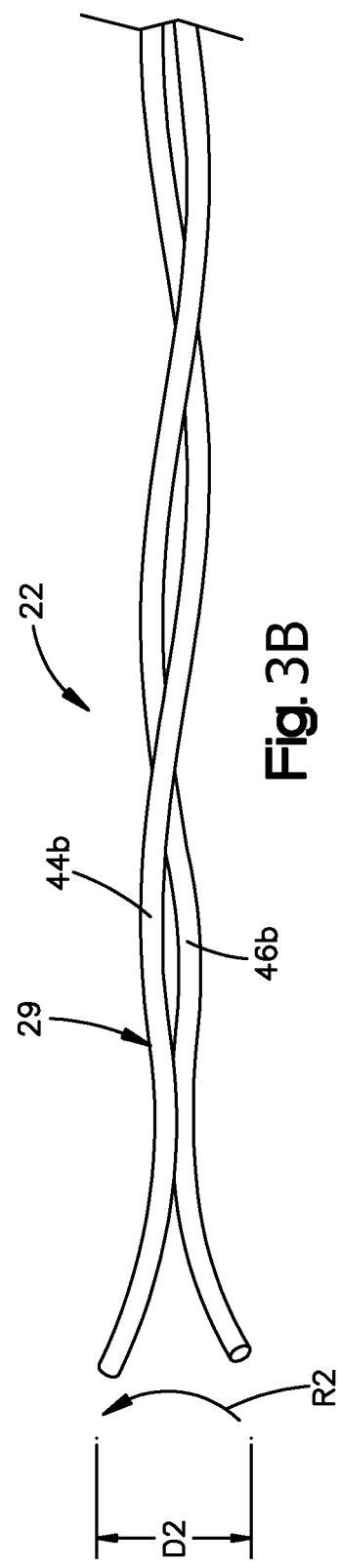

INTRAMEDULLARY FIXATION SYSTEM

CROSS-REFERENCE TO RELATED APPLICATIONS

The present application claims the benefit of U.S. Provisional Application Ser. No. 61/692,673, filed Aug. 23, 2012, U.S. Provisional Application Ser. No. 61/710,830, filed Oct. 8, 2012, and U.S. Provisional Application Ser. No. 61/786,937, filed Mar. 15, 2013, the entire disclosure of each aforementioned application is incorporated by reference into this application for all purposes. The entire disclosure of U.S. application Ser. No. 13/832,518, filed Mar. 15, 2013, is also incorporated by reference into this application for all purposes.

TECHNICAL FIELD

The present disclosure relates to the fields of bone implants and bone fixation devices.

BACKGROUND

Fractured bones (including so-called long bones such as femurs, tibias, fibulas, humeri, radii, ulnas, metacarpals, metatarsals, and phalanges, and the like) are conventionally stabilized by inserting an intramedullary rod or nail into the medullary canal of the fractured bone and inserting screws through the bone (in a direction transverse to the major axis of the nail) so as to engage with locking holes in the nail, thereby fixing the nail to the fractured bone across the fracture.

SUMMARY

In one embodiment, an intramedullary implant is configured to be inserted into the medullary canal of a fractured long bone. In accordance with one embodiment, an intramedullary implant system is configured to fix a first bone segment to a second bone segment that is separated from the first bone segment by a gap. The intramedullary implant system can include an intramedullary fixation member that defines at least first and second wire segments that each defines a proximal end and a free distal end. At least a select one of the first and second wire segments can be twisted about the other of the first and second wire segments in a first rotational direction so as to define an intersection that is disposed at least at one of the distal ends whereby the select wire segment crosses the other wire segment. The distal ends are sized to fit into a medullary canal of one of the first and second bone segments, such that a force applied to the distal end of the select wire segment along a second rotational direction that is substantially opposite the first rotational direction causes the distal end of the select wire segment to separate from the distal end of the other wire segment at the intersection, so as to thereby fix the distal end of the select wire segment to the one of the first and second bone segment.

BRIEF DESCRIPTION OF THE DRAWINGS

The summary, as well as the following detailed description, is further understood when read in conjunction with the appended drawings. For the purpose of illustrating the present disclosure, there are shown in the drawings example embodiments of the disclosure; however, the disclosure is not limited to the specific methods, compositions, and devices disclosed. In addition, the drawings are not necessarily drawn to scale. In the drawings:

FIG. 1A is a schematic side elevation view of an intramedullary implant system constructed in accordance with one embodiment, including an intramedullary fixation member and an anchor member, showing the fixation member in an insertion position;

FIG. 1B is a schematic top elevation view of the intramedullary implant system illustrated in FIG. 1A, showing the fixation member in a fixation position;

FIG. 1C is a cross-section view of the intramedullary implant system taken along lines 1C-1C in FIG. 1B;

FIG. 3A is an enlarged perspective view of a distal end of the fixation member shown in the insertion position;

FIG. 3B is an enlarged perspective view of a distal end of the fixation member in the insertion position;

DETAILED DESCRIPTION

Figure 2A:
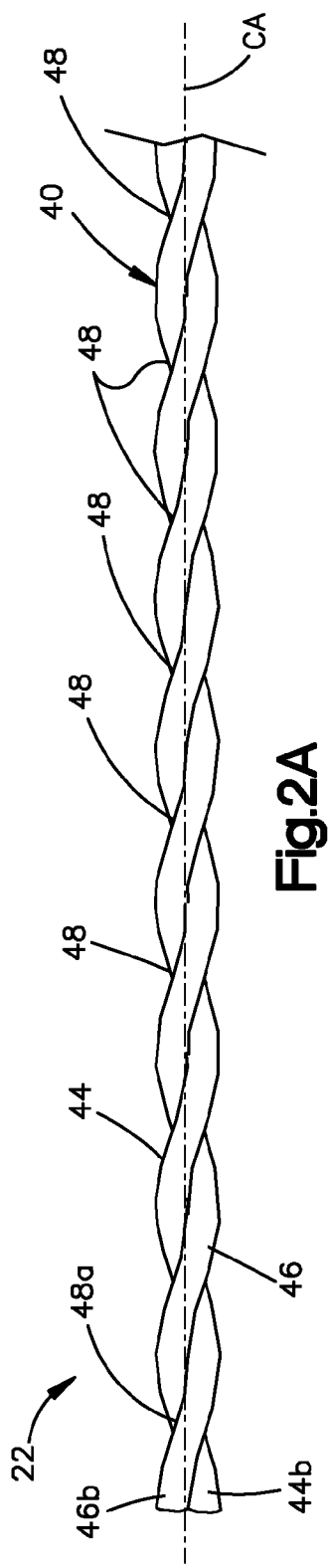
FIGS. 2A-C are various perspective views of fixation members including twisted wire segments.
Figure 2B:
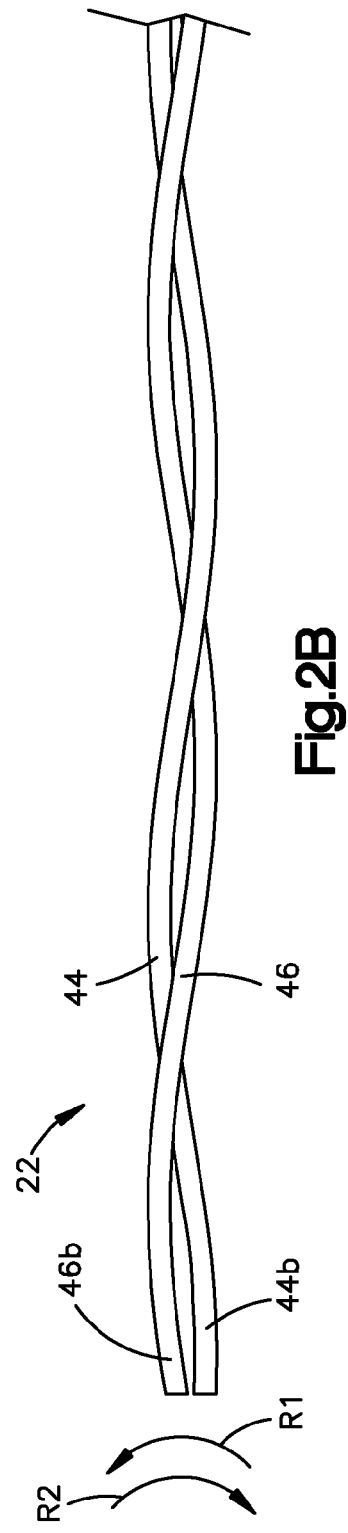
Figure 2C:
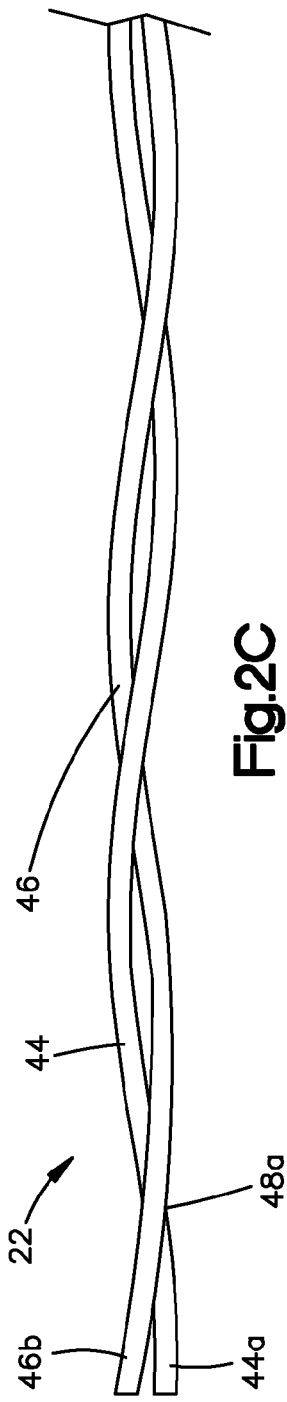

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the scope of the present disclosure. Also, as used in the specification including the appended claims, the singular forms "a," "an," and "the" include the plural, and reference to a particular numerical value includes at least that particular value, unless the context clearly dictates otherwise.

The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Referring initially to FIG. 1A, an intramedullary implant system 20 can include one or both of an intramedullary fixation member 22 and an anchor member 24. The intramedullary implant 22 is configured to stabilize a bone 28, which can be a long bone, having a boney wall 30, which can include a cancellous wall and a cortical wall that surrounds the cancellous wall. The bone 28 further defines a medullary canal 26 that is surrounded by the boney wall 30, and contains medullary bone material 31, which can include bone marrow, fragments of the boney wall 30, such as cortical wall fragments, and the like. Thus, it should be appreciated that the medullary bone material 31 can be highly viscous. The bone 28 defines a first or proximal bone segment 28a, a second or distal bone segment 28b spaced from the first bone segment 28a along a longitudinal direction L, and a defect 32 that is disposed between the first bone segment 28a and the second bone segment 28b. The defect 32 can be a fracture created by a traumatic event, an osteotomy, or can be the result of debridement of a joint of two discrete bones to be joined in an arthrodesis. Thus, in accordance with one embodiment, the defect 32 can be configured as a bone gap 34, such that the first and second bone segments 28a-b are spaced from each other by the bone gap 34.

The intramedullary fixation member 22 extends generally along a central axis CA, which can be a major axis as illustrated, and defines a proximal end 22a, a distal end 22b that is spaced from the proximal end 22a along the central axis CA, and an intermediate portion 22c that extends between the proximal end 22a and the distal end 22b. It can be said that the proximal end 22a is spaced from the distal end 22b in a proximal direction, and the distal end 22b is spaced from the proximal end 22a in a distal direction. The distal end 22b is configured to be inserted into a select one of the first and second bone segments 28a and 28b (the first bone segment 28a as illustrated) when the distal end 22b is in an insertion position, which thus defines an insertion position 27 of the fixation member 22. The distal end 22b is then driven along the medullary canal 26 of the select one of the first and second bone segments 28a and 28b, and into the medullary canal 26 of the other of the first and second bone segments 28a and 28b (the second bone segment 28b as illustrated). Once the distal end 22b is disposed in the medullary canal 26 of the second bone segment 28b, the intramedullary fixation member 22 is configured to be actuated to a fixation position 29 whereby the distal end 22b becomes coupled to the boney wall 30.

When the distal end 22b is coupled to the boney wall 30, the distal end 22b can be said to be substantially translatably fixed to the boney wall 30, such that movement of the distal end 22b along a proximal direction toward the first bone segment 28a causes one or both of the first and second bone segments 28a and 28b to move toward the other of the first and second bone segment 28a and 28b, thereby reducing the bone gap 34, as illustrated in FIG. 1B. It should be appreciated that the first and second bone segments 28a and 28b can be brought into anatomical alignment when or after the bone gap 34 is reduced. In accordance with the illustrated embodiment, the first bone segment 28a can be a diaphysis of a long bone and the second bone segment 28b can be a metaphysis of the long bone, and movement of the distal end 22b in the proximal direction causes the second bone segment 28b to move toward the first bone segment 28a. Referring to FIG. 1C, and as is described in more detail below, the anchor member 24 can be secured to the first bone segment 28b, and the intramedullary fixation member 22, for instance at the proximal end 22a, can be secured in the anchor member 24, such that the intramedullary implant system 20 is fixed to both the first bone segment 28a and the second bone segment 28b, which fixes the first and second bone segments 28a and 28b relative to each other and maintains the bone gap 34 in its reduced state.

Referring now to FIGS. 1A-2C, the intramedullary fixation member 22 includes at least one wire 40 that defines a plurality of wire segments, including a first wire segment 44 and a second wire segment 46. The first wire segment 44 extends along a length, and can define a proximal end 44a (see FIGS. 4A-B) and an opposed free distal end 44b that is spaced from the proximal end 44a along the length of the first wire segment 44, and an intermediate portion 44c that extends between the proximal end 44a and the distal end 44b, for instance from the proximal end 44a to the distal end 44b. Similarly, the second wire segment 46 extends along a length, and can define a proximal end 46a (see FIGS. 4A-B) and an opposed free distal end 46b that is spaced from the proximal end 46a along the length of the second wire segment 46, and an intermediate portion 46c that extends between the proximal end 46a and the distal end 46b, for instance from the proximal end 46a to the distal end 46b.

In accordance with one embodiment, the intramedullary fixation member 22 can be a single homogenous member, such that the first and second wire segments 44 and 46 can be integral and monolithic with each other, and attached to each other and coextensive at their respective proximal ends 44a and 46a. For instance, the intramedullary fixation member 22 can be a single wire, such as a Kirschner wire or K-wire, such that the first and second wire segments 44 and 46 are defined by a single K-wire. The K-wire can be made from any suitable biocompatible material, such as stainless steel or titanium, alloys thereof, and the like, and each wire segment can have any diameter as desired, for instance between approximately 0.5 mm and approximately 5 mm, or any alternative diameter, such that the wire segments 44 and 46 are flexible. Alternatively, the first and second wire segments 44 and 46 can be separate from each other, and thus non-monolithic with each other. For instance the first wire segment 44 can be defined by a first wire, such as a K-wire, and the second wire segment 46 can be defined by a second wire, such as a K-wire, that is different than the first wire. It should be appreciated that the intramedullary fixation member 22 can include any number of wire segments as desired, which can be integral and monolithic with each other or separate from each other as desired. Further, the wire 40 can be a twisted structure formed of two or more wires twisted together that define the wire 40 and/or wire segments. For instance, the wire segment 44 can be twisted structure of two or more wires, and the wire segment 46 can be a twisted structure of two or more wires. In addition, the wire 40 can be a braided structure formed of a plurality of wires, for instance at least three wires, that define the wire 40 and/or wire segments. Thus, the wire segment 44 can be a braided wire structure formed of three or more wires, and the wire segment 46 can be a braided wire structure formed of three or more wires.

At least a portion of at least one of the first and second wire segments 44 and 46 is twisted about at least a portion of at least one of the other of the first and second wire segments 44 and 46, such that the intramedullary fixation member 22 defines a twisted structure. For instance, at least one or more up to all of the proximal end 44a, the distal end 44b, and the intermediate portion 44c can be twisted about at least one or more up to all of the proximal end 46a, the distal end 46b, and the intermediate portion 46c, respectively. Alternatively or additionally, at least one or more up to all of the proximal end 46a, the distal end 46b, and the intermediate portion 46c can be twisted about at least one or more up to all of the proximal end 44a, the distal end 44b, and the intermediate portion 44c, respectively. In accordance with the illustrated embodiment, each of the first and second wire segments 44 and 46 is twisted, for instance substantially helically twisted, about the other of the first and second wire segments 44 and 46. In particular, at least a portion of the first wire segment 44 can be twisted about at least a portion of the second wire segment 46 in a first rotational direction R1 as it extends along the distal direction (e.g., along a direction from the proximal end 44a toward the distal end 44b), and at least a portion the second wire segment 46 can be twisted about at least a portion of the first wire segment 44 in the first rotational direction R1 as it extends along the distal direction (e.g., along a direction from the proximal end 46a toward the distal end 46b), such that the twisted portion each of the first and second wire segments 44 and 46 can define a helix having either a constant pitch or a variable pitch as desired. Further, it should be appreciated that the intramedullary fixation member 22 can include additional wire segments, for instance at least a first, second and third wire segments that are braided such that the twisted structure can further define a braided structure.

Thus, it should be appreciated the intramedullary fixation member 22 can define at least one intersection 48, such as a plurality of intersections 48 that are spaced along the central axis CA of the fixation member 22 and defined at locations, each intersection defined as a location whereby at least one of the first and second wire segments 44 and 46 crosses the other of the first and second wire segments 44 and 46, from one side of the wire segment to the other. Referring also to FIGS. 3A-B, the intramedullary fixation member 22 defines at least one distal intersection 48a that is disposed at least at one of the distal ends 44a and 46a, whereby the distal end of at least a select one of the wire segments 44 and 46 is twisted about the other of the first and second wire segments 44 and 46, for instance at the distal end of the other wire segment. It should be appreciated that the intramedullary fixation member 22 can define the insertion position 27, whereby the distal ends 44b and 46b of first and second wire segments 44 and 46 are spaced from each other a first distance D1 at the distal intersection 48a along a direction that is substantially perpendicular to the central axis CA of the fixation member 22 (said amount can be zero or greater than zero) such that the distal ends 44a and 46a are sized to fit into the medullary canal 26 of one of the first and second bone segments 28a and 28b.

When a separation force is applied to the distal end of the select wire segment, along a second rotational direction R2 that is substantially opposite the first rotational direction causes, the separation force causes the distal end of the select wire segment to separate from the distal end of the other wire segment at the distal intersection 48a, which actuates the intramedullary fixation member 22 to a fixation position 29 whereby the distal end of the select wire segment is coupled to the respective bone segment, such as translatably coupled to the respective bone segment, such as the second bone segment 28b. Thus, the distal ends 44b and 46b of first and second wire segments 44 and 46 are spaced from each other a second distance D2 at the distal intersection 48a along a direction that is substantially perpendicular to the central axis CA of the fixation member 22, the distance D2 greater than the distance D1 when the fixation member 22 is in the insertion position 27. Thus, when the fixation member 22 is in the fixation position 29, the distal end of the select wire segment can become coupled to the boney wall, including at least one or both of the cancellous wall and the cortical wall. Accordingly, movement of the intramedullary fixation member 22 in the proximal direction relative to the first bone segment 28a causes the second bone segment 28b to move toward the first bone segment 28a as described above. The separation force can be generated from the medullary bone material in the medullary canal that resists rotation of the distal ends 44a and 46a of the first and second wire segments 44 and 46 in the first rotational direction R1. It should be further appreciated that the distal ends 44a and 46a of both the first and second wire segments 44 and 46 can be twisted about the other at the distal intersection 48a, such that the separation force causes each of the distal ends 44a and 46a to separate from the other of the distal ends 44a and 46a, thereby causing both distal ends 44a and 46a to couple to the boney wall 30. In accordance with certain embodiments, the rotation in the first rotational direction R1 can cause the separation force to remove the distal intersection 48a, as illustrated in FIG. 3B.

With continuing reference to FIGS. 1A-2C, it should be appreciated that the first and second wire segments 44 and 46 are attached to each other at a location between their respective proximal ends 44a and 46a and the at least one distal intersection 48a. For instance, the first and second wire segments 44 and 46 can be attached to each other at least at one or more up to all of the plurality of intersections 48 that are disposed between the proximal ends 44a and 46a and the distal intersection 48a. For instance, the first and second wire segments 44 and 46 can be fused to each other at the at least one or more up to all of the intersections 48. In one example, the first and second wire segments 44 and 46 can be welded or soldered to each other. In accordance with the illustrated embodiment, all of the attached, for instance fused, intersections are disposed proximal with respect to the distal intersection 48a, so that the distal ends 44b and 46b can separate from each other while at least one location proximal of the distal ends 44b and 46b remain attached to each other. It should be appreciated that the first and second wire segments 44 and 46 are not attached to each other at the distal intersection 48a, such that the separation force is sufficient to causes the first and second wire segments 44 and 46 to separate from each other at the distal intersection 48a.

It should be further appreciated that the intramedullary fixation member 22 can define more than one intersection, for instance a second distal intersection or a plurality of distal intersections disposed adjacent the distal intersection 48a, that are configured to separate in response to the separation force. Furthermore, it should be appreciated that the first and second wire segments 44 and 46 can be attached to each other at one or more locations proximal with respect to the distal intersection 48a without intersecting at the one or more locations. For instance, the first and second wire segments 44 and 46 can extend substantially parallel to each other proximal of the distal intersection 48a, and can be fused (for instance, spot welded) to each other at one or more locations from the distal intersection to the proximal ends 44a and 46a, including the intermediate portions 44c and 46c and the proximal ends 44a and 46a.

Figure 4A:
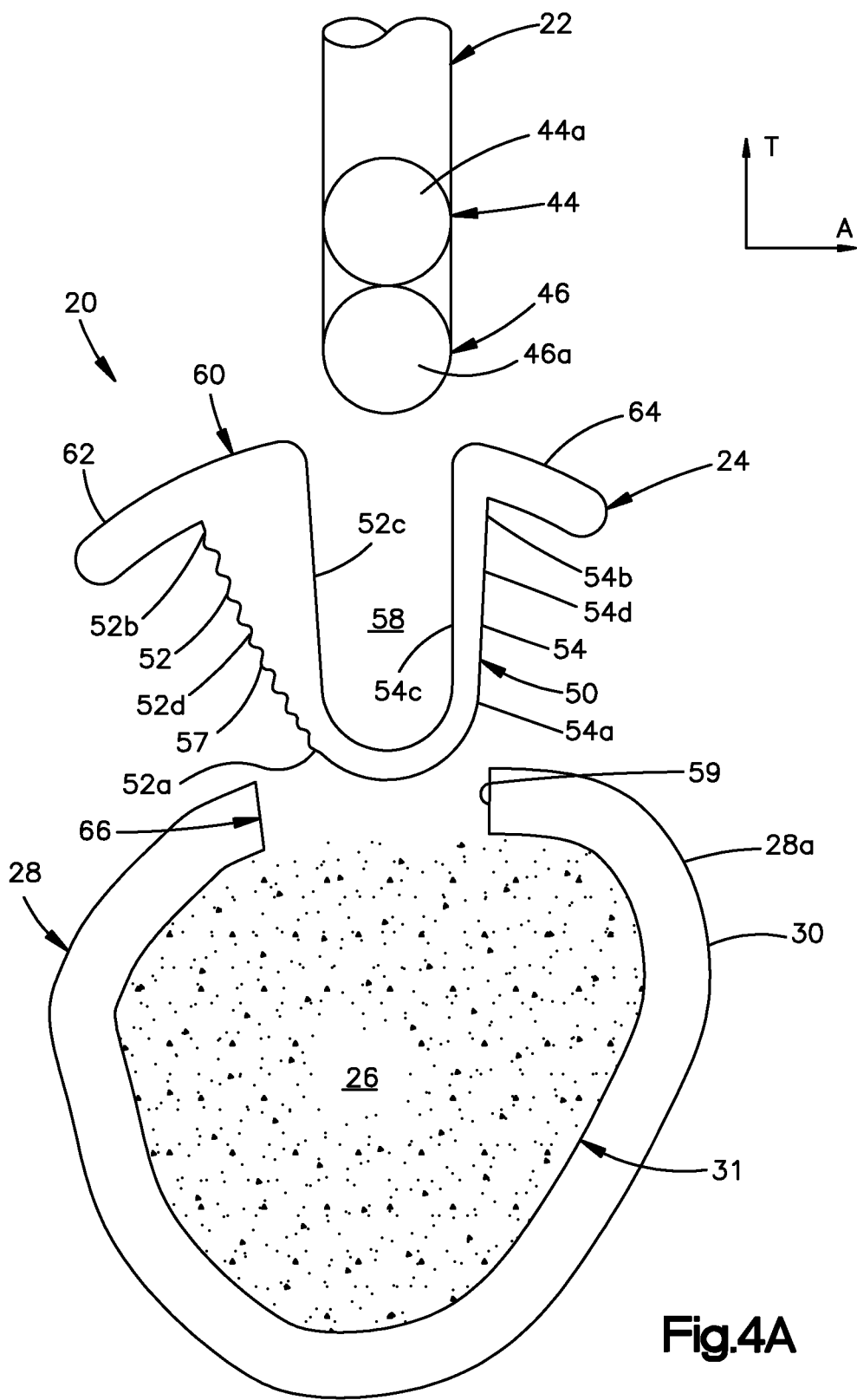
FIG. 4A is a schematic exploded view of the intramedullary implant system showing insertion of the fixation member into the anchor member, and insertion of the fixation member into an underlying bone.
Figure 4B:
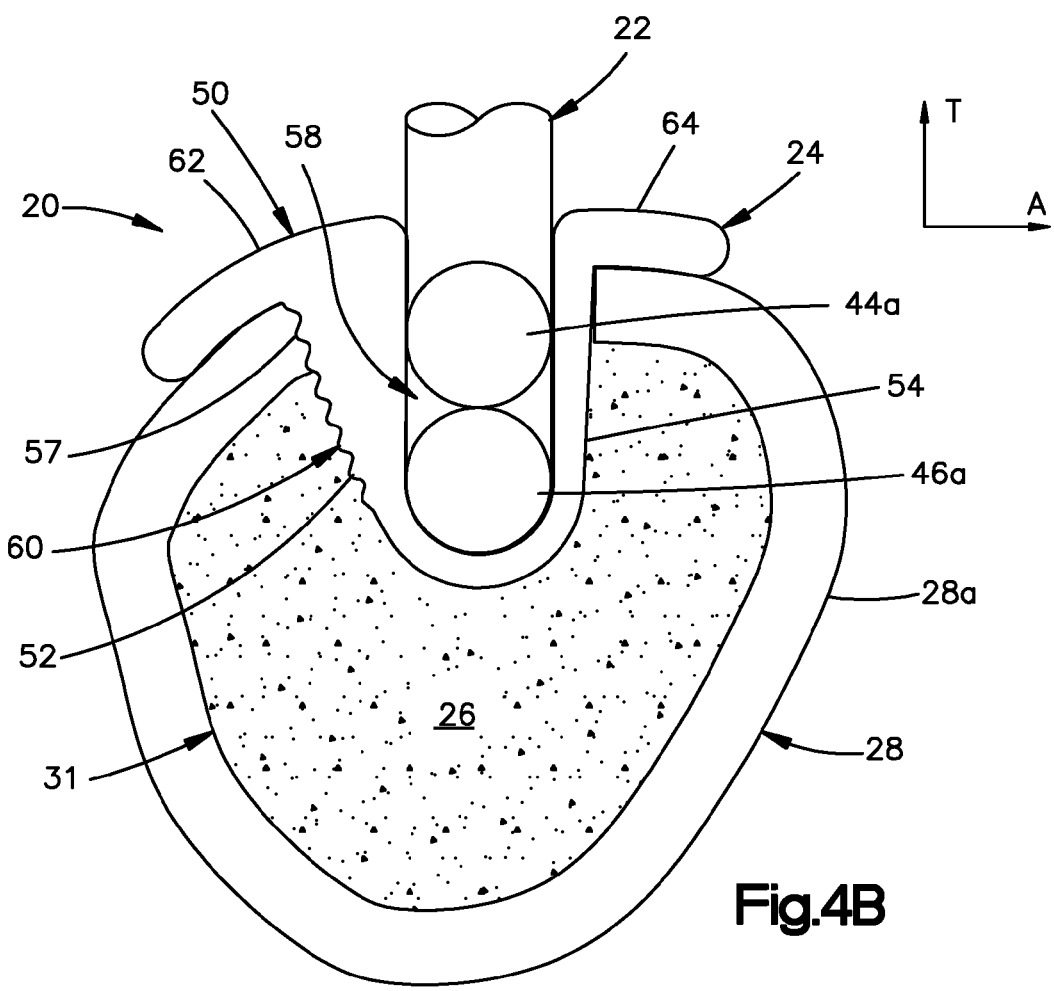
FIG. 4B is a schematic end elevation view of the intramedullary implant system illustrated in FIG. 4A, showing the fixation member inserted into the anchor member, and the fixation member inserted into the underlying bone.
Figure 4C:
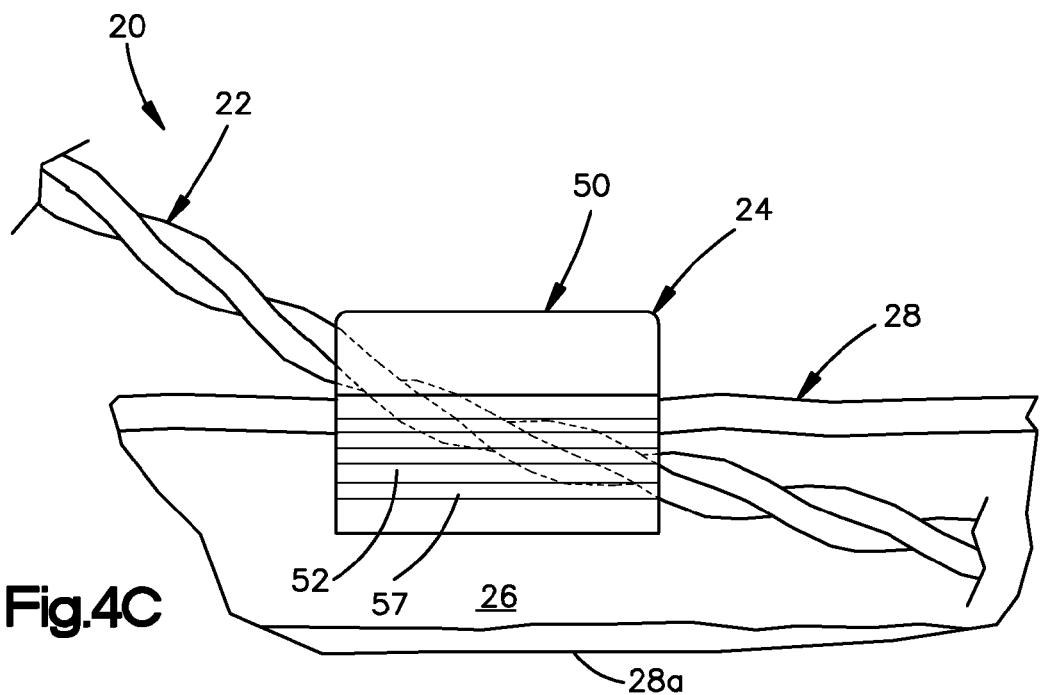
FIG. 4C is a schematic side elevation view of the intramedullary implant system illustrated in FIG. 4B.

Referring now also to FIGS. 4A-4C, the intramedullary implant system 20 can further include the anchor member 24 that is configured to attach to one of the first and second bone segments 28a and 28b, and is further configured to attach to the intramedullary fixation member 22. For instance, the anchor member 24 is configured to attach to the bone segment that initially receives the intramedullary fixation member 22 prior to moving the intramedullary fixation member across the bone gap 34. In accordance with the illustrated embodiment, the anchor member 24 is configured to be attached to the first bone segment 28a, and is further configured to be attached to the intramedullary fixation member 22, for instance at the proximal end 22a, while the distal end 22b is coupled to the second bone segment 28b, thereby fixing the first and second bone segments 28a and 28b with respect to relative movement along the longitudinal direction L.

In accordance with the illustrated embodiment, the anchor member 24 is configured as a fixation clip 50 that is configured to extend at least into or through the boney wall of the first bone segment 28a along a transverse direction T toward or into the medullary canal 26. For instance the transverse direction T can be substantially perpendicular to the longitudinal direction L. The fixation clip 50 can define first and second walls opposed walls 52 and 54 that are configured to be spaced from each other along a lateral direction A that is substantially perpendicular to the longitudinal direction L and the transverse direction T. The first and second walls 52 and 54 define respective proximal ends 52a and 54a and opposed respective free distal ends 52b and 54b. The proximal ends 52a and 54a can be are attached to each other at a hinge region 56 of the fixation clip 50, such that the first and second walls 52 and 54 are configured to resiliently flex toward and away from each other at the hinge region 56. Thus, at least one of the first and second walls 52 and 54 is compressible, for instance resiliently compressible, toward the other of the first and second walls 52 and 54. In accordance with the illustrated embodiment, the first and second walls 52 and 54 and the hinge region 56 can be integral and monolithic with each other, or can be separate and attached to each other.

The fixation clip 50 further defines a retention pocket 58 that can be least partially defined, for instance fully defined, between the first and second opposed walls 52 and 54 along the lateral direction A. Thus, the fixation clip 50 can include a fixation clip body 60 that includes the first and second walls 52 and 54 and the hinge region 56, such that the retention pocket 58 extends at least into the fixation clip body 60 along the longitudinal direction L at a location between the first and second walls 52 and 54. The retention pocket 58 can, for instance, extend through the fixation clip body 60 along the longitudinal direction L at a location between the first and second walls 52 and 54. The retention pocket 58 can further extend down into the fixation clip body 60 along the transverse direction T from the distal ends 52b and 52c toward the hinge region 56, such that the hinge region 56 can define a seat for the fixation member 22 as desired when the fixation member 22 is disposed in the retention pocket 58.

Each of the first and second walls 52 and 54 thus defines a respective inner surface 52c and 54c that face each other and at least partially define the retention pocket 58. Each of the first and second walls 52 and 54 further defines a respective outer surface 52d and 54d that faces opposite the corresponding inner surface 52c and 54c, and is thus configured to face and abut the bone 28, for instance at the first bone segment 28a. At least one of the outer surfaces 52d and 54d can be ridged so as to present a textured surface that frictionally engages a surface of the bone 28 when the fixation clip 50 is inserted into the bone 28 so as to resist migration of the fixation clip 50 out of the bone 28. The outer surface 52d of the first wall 52 is illustrated as including ridges 57.

The fixation clip body 60, and thus the fixation clip 50, can further define at least one stop member such as first and second stop members 62 and 64 that project outward from the respective first and second walls 52 and 54 away from the retention pocket 58. The stop members 62 and 64 can define a curvature configured to match the curvature of the bone 28, such that the stop members 62 and 64 abut the outer surface of the bone 28 when the fixation clip 50 is inserted into the bone 28.

During operation, referring to FIGS. 1A-C and 4A-4C, an opening 66 can be created in the first bone segment 28a that can extend through the boney wall 30 and into the medullary canal 26. Next, the distal end 22b of the intramedullary fixation member 22 can be inserted through the opening and into the medullary canal while the intramedullary fixation member 22 is in the fixation position 27. The intramedullary fixation member 22 can be inserted along a direction such that the central axis CA is minimally offset with respect to the longitudinal axis L of the bone 28. The intramedullary fixation member 22 can be moved along the distal direction toward the second bone segment 28b through the medullary canal 26 of the first bone segment 28a until the distal end 22b of the intramedullary fixation member 22 crosses the bone gap 34 and enters the medullary canal 26 of the second bone segment 28b. Any suitable medical imaging can detect the position of the second bone segment 28b. Alternatively or additionally, tactile feedback can inform the surgeon that the distal end 22b is in the medullary canal 26 of the second bone segment 28b.

Once the distal end 22b of the intramedullary fixation member 22 is in a desired positioned in the medullary canal 26 of the second bone segment 28b, the intramedullary fixation member 22 can be rotated in the first rotational direction R1 (see FIGS. 3A-B) so as to actuate the intramedullary fixation member 22 from the insertion position 27 to the fixation position 29. In particular, a portion of the intramedullary fixation member 22, such as the proximal end 22a alone or in combination with a portion of the intermediate portion 22c, can extend out the opening 66 and receive a rotational force in the first rotational direction R1, which is communicated to the distal end 22b of the intramedullary fixation member 22.

As the distal end 22b rotates in the first rotational direction R1, the medullary bone material 31 provides a force that resists motion of the distal end 22b in the first rotational direction R1, and thus applies the resistive separation force in the second rotational direction R2 to the distal end 22b. Thus, the separation force causes the distal end or ends 44b, 46b of at least one or both of the first and second wire segments 44 and 46 to separate from the other of the distal end 44b, 46b at the distal intersection 48a. For instance, the separation of the distal ends 44b and 46b at the distal intersection 48a can remove the distal intersection altogether. The distal ends 44b and 46b separate from each other along a direction substantially perpendicular to the longitudinal axis L of the bone 28 until the distal ends 44b and 46b contact the boney wall 30 of the second bone segment 28b and, either through friction or mechanical interference or both, become coupled to the boney wall 30. For instance, rotation of the distal end 22b in the first rotational direction R1 can cause the distal ends 44b and 46b of the first and second wire segments 44 and 46 to score into the boney wall 30, including the cancellous wall and the cortical wall. Accordingly, subsequent movement of the intramedullary fixation member 22 in the proximal direction causes the distal ends 44b and 46b of the wire segments 44 and 46 to move in the proximal direction toward the first bone segment 28a. Because the distal ends 44b and 46b are coupled to the boney wall 30, movement of the distal ends 44b and 46b in the proximal direction causes the second bone segment 28b to move in the proximal direction toward the first bone segment 28a.

If it is desired to remove the intramedullary fixation member 22 from the medullary canal 26, for instance after bone fixation, the intramedullary fixation member 22 can be rotated in the second rotational direction R2, which causes the medullary bone material 31 to apply a counter force against the distal ends 44b and 46b that biases the distal ends 44b and 46b toward each other and away from the boney wall 30. Additionally, the proximal end 22a of the intramedullary fixation member 22 can be grasped, for instance with a gripping instrument such as pliers, forceps, calipers, or the like, so as to apply a proximally-directed force, alone or in combination with rotation and, perhaps, impacting with a mallet or the like, so as to free the distal ends 44*b* and 46*b* from the boney wall 30.

Once the bone gap 34 has been reduced, the proximal end 22*a* of the intramedullary fixation member 22 can be secured to the first bone segment 28*a* so as to prevent the first and second bone segments 28*a* and 28*b* from separating from each other. For instance, the proximal ends 46*a* and 46*a* can be inserted into the retention pocket 58, and the wire segments 44 and 46 can be severed if desired such that the proximal ends 44*a* and 46*a* terminate in the retention pocket 58. The proximal ends 44*a* and 46*a* are then placed in the retention pocket 58 such that one of the proximal ends 44*a* and 46*a* can be disposed adjacent the hinge region 56, for instance can rest against the hinge region 56, and the other of the proximal ends 44*a* and 46*a* is disposed adjacent the one of the proximal ends 44*a* and 46*a* along the transverse direction. Thus, the retention pocket 58 can define a width in the lateral direction A that is sufficient to receive the proximal ends 44*a* and 46*a* that are stacked along the transverse direction T.

Once the proximal ends 44*a* and 46*a* are disposed in the retention pocket 58, the fixation clip 50 is inserted in the opening 66. Prior to insertion into the opening, the outer surfaces 52*d* and 54*d* are separated a first distance along the lateral direction A adjacent the hinge region 56, the distance being less than the dimension of the opening 66 along the lateral direction A. The outer surfaces 52*d* and 54*d* are separated a second distance along the lateral direction A at a location adjacent the respective stop members 62 and 64, the second distance greater than the dimension of the opening 66 along the lateral direction A. Accordingly, as the fixation clip 50 is inserted into the opening 66, the first and second walls 54 and 56 ride along an internal surface 59 of the first bone segment 58*a* that defines the opening 66, which causes the first and second walls 54 and 56 to compress toward each other, and compress against the wire segments 44 and 46 until the stop members 62 and 64 abut the outer surface of the boney wall 30. Because at least one of the outer surfaces 54*d* and 56*d* can be ridged, the corresponding at least one of the first and second side walls 54 can frictionally engage the internal surface 59 of the first bone segment 58*a*. Further, because the inner surfaces 54*c* and 56*c* are compressed against the wire segments 44 and 46, the retention clip 50 fixes the intramedullary fixation member 22 with respect to the first bone segment 28*a*.

If desired, the intramedullary fixation system 20 can be removed from the bone 58 after the first and second bone segments 58*a* and 58*b* have been fixed to each other across the defect 32. For instance, in certain cases, it is intended that the intramedullary fixation system 20 will remain in the bone 58 after the first and second bone segments 28*a* and 28*b* have fused to each other across the defect 32. In other cases, the intramedullary fixation system 20 may be removed after the first and second bone segments 28*a* and 28*b* have fused to each other across the defect 32. For instance, the proximal ends 44*a* and 46*a* can be removed from the retention pocket 58, and withdrawn from the medullary canal 26 through the opening 66. Next, the first and second walls 54 and 56 can be compressed toward each other to remove the ridged outer surface from interference with the first bone segment 58*a*, and the fixation clip 50 can be removed from the first bone segment 58*a*.

The intramedullary fixation system 20 can thus provide a method for stabilizing the bone 28 having a first bone segment 28*a*, the second bone segment 28*b*, and the defect 32 disposed between the first and second bone segments 28*a* and 28*b*. The method can include the step of inserting an implant, such as the intramedullary fixation member 22, into the medullary canal 26 of the bone 58 at the first bone segment 58*a*, the intramedullary fixation member 22 including at least first and second wire segments 44 and 46 that each define a proximal end 44*a* and 46*a*, respectively, and a free distal end 44*b* and 46*b*, respectively, the first wire segment 44 twisted about the second wire segment 46 in a rotational direction, such as the first rotational direction R1, so as to define at least one intersection 48, such as the distal intersection 48*a*, whereby the first wire segment 44 crosses the second wire segment 46. The method can further include the step of advancing the intramedullary fixation member 22 along the medullary canal 26 until the distal ends 44*b* and 46*b* are disposed in the medullary canal 26 of the second bone segment 28*b*. The method can include the step of rotating the intramedullary fixation member 22 in the rotation direction R1 so as to cause the distal ends 44*b* and 46*b* to separate from each other and couple to a boney wall 30 of the second bone segment 58*b* in response to a resistive force against rotation of the implant in the rotational direction R1. In this regard, it should be appreciated that the rotation in the first rotational direction R1 should be at a sufficient speed such that the opposed separation force is sufficient to separate the distal ends 44*b* and 46*b*.

The method can further include the step of, after the rotating step, drawing the intramedullary fixation member 22 along a proximal direction from the distal ends 44*b* and 46*b* toward the proximal ends 44*a* and 46*a* so as to correspondingly draw the second bone segment 58*b* toward the first bone segment 58*a*. The method can further include the step of, after the drawing step, anchoring the proximal ends 44*a* and 46*a* to an anchor member 24, such as the fixation clip 50, that is coupled to the bone 58. The method can further include the step of creating the opening 66 in the first bone segment 58*a*, and inserting the intramedullary fixation member 22 through the opening 66 and into the medullary canal 26 of the bone 28 at the first bone segment 58*a*. The method can further include the step of attaching the anchor member 24 to the first bone segment 58*a*, such that at least a portion of the anchor member 24 extends into the opening 66. The method can further include the step of, after the rotating step, rotating the first and second proximal ends 44*a* and 46*a* in a second direction R2 opposite the rotation direction so as to draw the distal ends of the first and second wire segments toward each other, thereby decoupling the distal ends from the boney wall of the second bone segment. The method can further include the steps of, before, after, or during the rotation in the second direction R2, grasping the intramedullary fixation member 22, for instance at the proximal end 22*a*, and applying a proximally-directed force, alone or in combination with impacting the intramedullary fixation member 22 with a mallet or the like, so as to free the distal ends 44*b* and 46*b* from the boney wall 30. The method can further include the step, after the second rotating step, of withdrawing the intramedullary fixation system 20 from the bone 58.

The foregoing description is provided for the purpose of explanation and is not to be construed as limiting the invention. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the invention is not intended to be limited to the particulars disclosed herein. Those skilled in the relevant art, having the benefit of the teachings of this specification, may effect numerous modifications to the invention as described herein, and changes may be made without departing from the spirit and scope of the invention as defined by the appended claims.

What is claimed:

1. An intramedullary implant system configured to fix a first bone segment to a second bone segment that is separated from the first bone segment by a gap, the intramedullary implant system comprising:
    an intramedullary fixation member that defines at least first and second wire segments that each define a proximal end and a free distal end, at least a select one of the first and second wire segments is twisted about the other of the first and second wire segments in a first rotational direction so as to define an intersection that is disposed at least at one of the distal ends whereby the select wire segment crosses the other wire segment,
    wherein the distal ends are sized to fit into a medullary canal of one of the first and second bone segments, and the distal end of the select wire segment is separable from the distal end of the other of the first and second wire segments 1) in response to a force applied to the distal end of the select wire segment along a second rotational direction that is substantially opposite the first rotational direction, and 2) a sufficient distance so as to thereby fix the distal end of the select wire segment to the one of the first and second bone segments.

2. The intramedullary implant system as recited in claim 1, wherein rotation of the intramedullary fixation member along the first rotational direction causes medullary bone material in the medullary canal to apply the force along the second rotational direction.

3. The intramedullary implant system as recited in claim 2, wherein the intersection is a distal intersection whereby the distal end of the select wire segment crosses the distal end of the other wire segment, and the rotation causes the distal end of the select segment to separate from the distal end of the other wire segment at the distal intersection.

4. The intramedullary implant system as recited in claim 3, wherein the rotation causes the distal intersection to be removed.

5. The intramedullary implant system as recited in claim 3, wherein the first and second wire segments are attached to each other at a location between the proximal ends and the distal intersection.

6. The intramedullary implant system as recited in claim 5, wherein the intramedullary fixation member defines a plurality of intersections whereby the select wire segment crosses the other wire segment at locations between the proximal ends and the distal intersection, and the wire segments are attached to each other at least at one of the plurality of intersections.

7. The intramedullary implant system as recited in claim 6, wherein the first and second wire segments are fused to the each other at the at least one of the plurality of intersections.

8. The intramedullary implant system as recited in claim 7, wherein the first and second wire segments are welded or soldered to each other at the at least one of the plurality of intersections.

9. The intramedullary implant system as recited in claim 7, wherein the second wire segment is twisted about the first wire segment in the first rotational direction.

10. The intramedullary implant system as recited in claim 9, wherein the first and second wire segments are substantially helically twisted about each other so as to define the plurality of intersections, whereby the first and second wire segments are fused to each other at least at some of the intersections, and all of the fused intersections are disposed proximal with respect to the distal intersection.

11. The intramedullary implant system as recited in claim 1, wherein the first and second wire segments are monolithic with each other and attached to each other at their respective proximal ends.

12. The intramedullary implant system as recited in claim 11, wherein the first and second wire segments are defined by a single k-wire.

13. The intramedullary implant system as recited in claim 1, wherein the first and second wire segments are separate from each other.

14. The intramedullary implant system as recited in claim 13, wherein each of first and second wire segments is a k-wire.

15. The intramedullary implant system as recited in claim 1, wherein the first and second wire segments are braided in the first rotational direction.

16. The intramedullary implant system as recited in claim 1, further comprising an anchor member configured to attach to 1) one of the first and second bone segments, and 2) the intramedullary fixation member.

17. The intramedullary implant system as recited in claim 16, wherein the anchor member comprises a fixation clip that defines first and second walls that at least partially define a retention pocket configured to receive the first and second wire segments.

18. The intramedullary implant system as recited in claim 17, wherein at least one of the first and second walls is compressible toward the other of the first and second walls.

19. The intramedullary implant system as recited in claim 17, wherein at least one of the first and second walls defines a ridged outer surface.

20. The intramedullary implant system of claim 1, wherein the first and second wire segments are configured such that a force applied to the distal ends of the first and second wire segments along the second rotational direction causes the distal ends of the first and second wire segments to separate from one another at the intersection.

21. A method of stabilizing a bone having a first bone segment, a second bone segment, and a defect disposed between the first and second bone segments, the method comprising the steps of:
    inserting an implant into a medullary canal of the bone at the first bone segment, the implant including at least first and second wire segments that each define a proximal end and a free distal end, the first wire segment twisted about the second wire segment in a rotational direction so as to define at least one intersection whereby the first wire segment crosses the second wire segment,
    advancing the implant along the medullary canal until the distal ends of the first and second wire segments are disposed in the second bone segment; and
    rotating the implant in the rotational direction so as to cause the distal ends to separate from each other at the intersection and couple to a boney wall of the second bone segment in response to a resistive force against rotation of the implant in the rotational direction.

22. The method as recited in claim 21, further comprising the step of, after the rotating step, drawing the implant along a proximal direction from the distal ends toward the proximal ends so as to correspondingly draw the second bone segment toward the first bone segment.

23. The method as recited in claim 22, further comprising, after the drawing step, anchoring the proximal ends to an anchor member that is coupled to the bone.

24. The method as recited in claim 23, further comprising creating an opening in the first bone segment, and inserting the implant through the opening and into the medullary canal of the bone at the first bone segment.

25. The method as recited in claim 24, further comprising attaching the anchor member to the first bone segment, such that at least a portion of the anchor member extends into the opening.

26. The method as recited in claim 24, further comprising, after the rotating step, rotating the first and second proximal ends in a second direction opposite the rotational direction so as to draw the distal ends of the first and second wire segments toward each other, thereby decoupling the distal ends from the boney wall of the second bone segment.

27. The method as recited in claim 26, further comprising, after the second rotating step, withdrawing the implant from the bone.

\* \* \* \* \*